United States Patent
Wang et al.

(10) Patent No.: US 10,068,328 B2
(45) Date of Patent: Sep. 4, 2018

(54) SPARSE ITERATIVE PHASE CORRECTION FOR MR PARTIAL FOURIER RECONSTRUCTION

(71) Applicant: Siemens Healthcare GmbH, Munich (DE)

(72) Inventors: Qiu Wang, Princeton, NJ (US); Esther Raithel, Dormitz (DE)

(73) Assignee: Siemens Healthcare GmbH, Erlangen (DE)

( * ) Notice: Subject to any disclaimer, the term of this patent is extended or adjusted under 35 U.S.C. 154(b) by 479 days.

(21) Appl. No.: 14/978,100

(22) Filed: Dec. 22, 2015

(65) Prior Publication Data

US 2017/0178318 A1 Jun. 22, 2017

(51) Int. Cl.
*G06T 7/00* (2017.01)
*G06T 11/00* (2006.01)
(Continued)

(52) U.S. Cl.
CPC ............ *G06T 7/0012* (2013.01); *A61B 5/055* (2013.01); *A61B 5/7257* (2013.01);
(Continued)

(58) Field of Classification Search
CPC ....... G06T 7/00; G06T 7/0002; G06T 7/0012; G06T 2207/10088; G06T 2207/20056; G06T 2207/30004; G06T 3/00; G06T 3/40; G06T 3/4053; G06T 3/4076; G06T 11/008; G06T 2211/00; G06T 2211/40; G06T 2211/424; G06F 17/14; G06G 7/1921; G03H 1/16; G10H 2250/235; G01R 23/16; G01R 33/4818; G01R 33/4833; G01R 33/4835; G01R 33/4838; A61B 5/00; A61B 5/05; A61B 5/055; A61B 5/7257
(Continued)

(56) References Cited

U.S. PATENT DOCUMENTS 4,853,635 A 8/1989 Cuppen
5,084,818 A * 1/1992 Machida ............ G01R 33/4833
324/307
(Continued)

OTHER PUBLICATIONS

Noll, D.C., et al, "Homodyne detection in magnetic resonance imaging", IEEE Transactions of Medical Imaging, 1991, vol. 10, p. 154-163.
(Continued)

*Primary Examiner* — Hoai-An D Nguyen

(57) ABSTRACT

A method for sparse iterative phase correction for Magnetic Resonance (MR) partial Fourier reconstruction includes acquiring a partial Fourier k-space dataset using an MR scanner and estimating, by a control computer, a coil sensitivity map associated with the MR scanner from fully sampled k-space center. The control computer extracts a symmetrically sampled k-space center dataset from the partial Fourier k-space dataset and determines a low-resolution image based on the symmetrically sampled k-space center dataset and the coil sensitivity map. The control computer also determines phase corresponding to the low-resolution image. An iterative reconstruction process may then be applied to generate an image based on the partial Fourier k-space dataset. This iterative reconstruction process applies a Fast Iterative Shrinkage Thresholding Algorithm (FISTA) with phase correction based on the phase corresponding to the low-resolution image.

20 Claims, 11 Drawing Sheets

(51) Int. Cl.
*A61B 5/00* (2006.01)
*A61B 5/055* (2006.01)
*G01R 33/483* (2006.01)

(52) U.S. Cl.
CPC ........ *G01R 33/4833* (2013.01); *G06T 11/008* (2013.01); *G06T 2207/10088* (2013.01); *G06T 2207/30004* (2013.01)

(58) Field of Classification Search
USPC ....... 324/300, 307, 309, 76.11, 76.12, 76.19, 324/76.21
See application file for complete search history.

(56) References Cited

U.S. PATENT DOCUMENTS

| | | | | |
|---|---|---|---|---|
| 6,393,313 | B1* | 5/2002 | Foo | A61B 5/055 324/307 |
| 6,975,113 | B1* | 12/2005 | Gurr | G01R 33/56375 324/307 |
| 2007/0085538 | A1* | 4/2007 | Hinks | G01R 33/56341 324/309 |
| 2010/0272336 | A1* | 10/2010 | Taniguchi | A61B 5/0555 382/131 |
| 2015/0253408 | A1* | 9/2015 | Grodzki | G01R 33/307 324/309 |
| 2015/0310641 | A1* | 10/2015 | Purdy | G01R 33/565 382/131 |

OTHER PUBLICATIONS

McGibney, G., et al. "Quantitative evaluation of several partial Fourier reconstruction algorithms used in MRI", Magnetic Resonance in Medicine, 1993, vol. 30, p. 51-59.

Clayton, D. B., and R. Bammer. "Methods for SENSE reconstruction with partial k-space acquisition." Proc. Intl. Soc. Mag. Reson. Med. vol. 13. 2005.

Doneva, M., et al. "Partial Fourier compressed sensing." Proc. Intl. Soc. Mag. Reson. Med. vol. 18. 2010.

Li, G., et al., "A phase constrained reconstruction method in compressed sensing", Proceedings of the 22nd Annual Meeting of ISMRM, 2014.

* cited by examiner

Algorithm 1 $x = \text{mFISTA-PC}(y, A, L, \lambda, x_0, p)$ $s = x_0$
$\alpha_1 = 1$
for $k = 1$ to $K$ do
  $g = A^H(y - As)$
  $x_{k+0.5} = s + \frac{1}{L}g$
  $\hat{x} = \text{Proximal Algorithm}(x_{k+0.5}, W, \frac{\lambda}{L}, 1)$
  $x_{k+1} = |\hat{x}| * p$
  $\alpha_{k+1} = \frac{1 + \sqrt{1 + 4\alpha_k^2}}{2}$
  $s = x_{k+1} + \frac{\alpha_k - 1}{\alpha_{k+1}}(x_{k+1} - x_k)$
end for

*Fig. 3*

Algorithm 1 $x = \text{mFISTA-APC}(y, A, L, \lambda, x_0, p)$ $s = x_0$
$\alpha_1 = 1$
for $k = 1$ to $K$ do
    $g = A^H(y - As)$
    $x_{k+0.5} = s + \frac{1}{L}g$
    $\hat{x} = \text{Proximal Algorithm}(x_{k+0.5}, \mathbf{W}, \frac{\lambda}{L}, 1)$
    if $k <= 10$ then
        $x_{k+1} = |\hat{x}| * p$
    end if
    $\alpha_{k+1} = \frac{1 + \sqrt{1 + 4\alpha_k^2}}{2}$
    $s = x_{k+1} + \frac{\alpha_k - 1}{\alpha_{k+1}}(x_{k+1} - x_k)$
end for

*Fig. 4*

SPARSE ITERATIVE PHASE CORRECTION FOR MR PARTIAL FOURIER RECONSTRUCTION

TECHNOLOGY FIELD

The present invention relates generally to methods, systems, and apparatuses for performing Magnetic Resonance Imaging (MRI) partial Fourier image reconstruction using sparse iterative phase correction techniques. The disclosed techniques may be applied to reduce scan time in various MRI applications.

BACKGROUND

Partial Fourier has been a popular Magnetic Resonance (MR) image acquisition technique where the k-space samples are only acquired from part of the k-space, whereas the respective conjugate-symmetric points do not have to be acquired. Partial k-space acquisitions are often used for speedup, but this technique also reduces the smallest possible effective echo time, which can be quite long for a high resolution fully symmetric acquisition with long echo trains. When combined with parallel imaging and an efficient reconstruction algorithm, such technique has shown advantage in high-resolution imaging, allowing both fast acquisition and flexible choice of the acquisition protocol parameters.

However, due to system imperfections, noise, blood flow, or other perturbations, the acquired MR image is not exactly real-valued, which is the condition for conjugate-symmetry. Without a correction of the residual phase, resulting images are blurry and can contain ringing artifacts. Therefore, Partial Fourier reconstruction requires some kind of phase estimation/correction in order to optimize the quality of reconstructed images.

SUMMARY

Embodiments of the present invention address and overcome one or more of the above shortcomings and drawbacks, by providing methods, systems, and apparatuses related to a phase correction process suitable for use in a sparse iterative reconstruction algorithm. The process enables the combination of partial Fourier acquisition, sparse sampling patterns and sparse iterative reconstruction, leading to superior scan speedup compared to conventional MR acquisition techniques.

According to some embodiments of the present invention, a method for sparse iterative phase correction for Magnetic Resonance (MR) partial Fourier reconstruction includes acquiring a partial Fourier k-space dataset using an MR scanner (in phase-encoding or frequency-encoding directions). A control computer estimates a coil sensitivity map associated with the MR scanner from fully sampled k-space center. The control computer extracts a symmetrically sampled k-space center dataset from the partial Fourier k-space dataset and determines a low-resolution image based on the symmetrically sampled k-space center dataset and the coil sensitivity map. The control computer also determines phase corresponding to the low-resolution image. An iterative reconstruction process may then be applied to generate an image based on the partial Fourier k-space dataset. This iterative reconstruction process applies a Fast Iterative Shrinkage Thresholding Algorithm (FISTA) with phase correction based on the phase corresponding to the low-resolution image. In some embodiments, the iterative reconstruction process uses the aforementioned low-resolution image as an initial estimate for the image.

In some embodiments of the aforementioned method, a proximal operator (e.g., using a Chambolle-Pock or Dykstra algorithm) is applied during each respective iteration of the iterative reconstruction process to determine an updated estimate for the image. Then, a phase term in the updated estimate from the image may be replaced with the phase corresponding to the low-resolution image. Rather than performing this replacement during every iteration, in some embodiments, the replacement only occurs for certain iterations (e.g., the first pre-determined number of iterations).

According to other embodiments of the present invention, an article of manufacture for sparse iterative phase correction for MR partial Fourier reconstruction comprises a non-transitory, tangible computer-readable medium holding computer-executable instructions for performing the aforementioned method, with or without the additional features discussed above.

According to other embodiments of the present invention, a system for sparse iterative phase correction for MR partial Fourier reconstruction comprises an imaging device and a central computer. The imaging device comprises coils which are configured to acquire a partial Fourier k-space dataset acquired using a magnetic resonance imaging device. The central computer is configured to apply an iterative reconstruction process to generate an image based on the partial Fourier k-space dataset over a plurality of iterations. This iterative reconstruction process applies a FISTA with phase correction performed during at least a portion of the plurality of iterations. Additionally, in some embodiments, the control computer is further configured to estimate a coil sensitivity map associated with the imaging device, extract a symmetrically sampled k-space center dataset from the partial Fourier k-space dataset, and determine (a) a low-resolution image based on the symmetrically sampled k-space center dataset and the coil sensitivity map; and (b) phase corresponding to the low-resolution image. This phase may then be used for phase correction performed during each of the iterations.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 3 illustrates an algorithm for mFISTA with Phase Correction (mFISTA-PC), according to some embodiments;

FIG. 4 illustrates an algorithm for mFISTA with attenuated Phase Correction (mFISTA-APC), according to some embodiments;

DETAILED DESCRIPTION OF ILLUSTRATIVE EMBODIMENTS

The following disclosure describes the present invention according to several embodiments directed at methods, systems, and apparatuses related to sparse iterative phase correction for use in Magnetic Resonance Imaging (MRI) partial Fourier applications. The techniques described herein may be applied, for example to conventional sequences such as Sampling Perfection with Application optimized Contrasts using different flip angle Evolution. (SPACE) to reduce scan times associated with imaging with the sequence.

Figure 1:
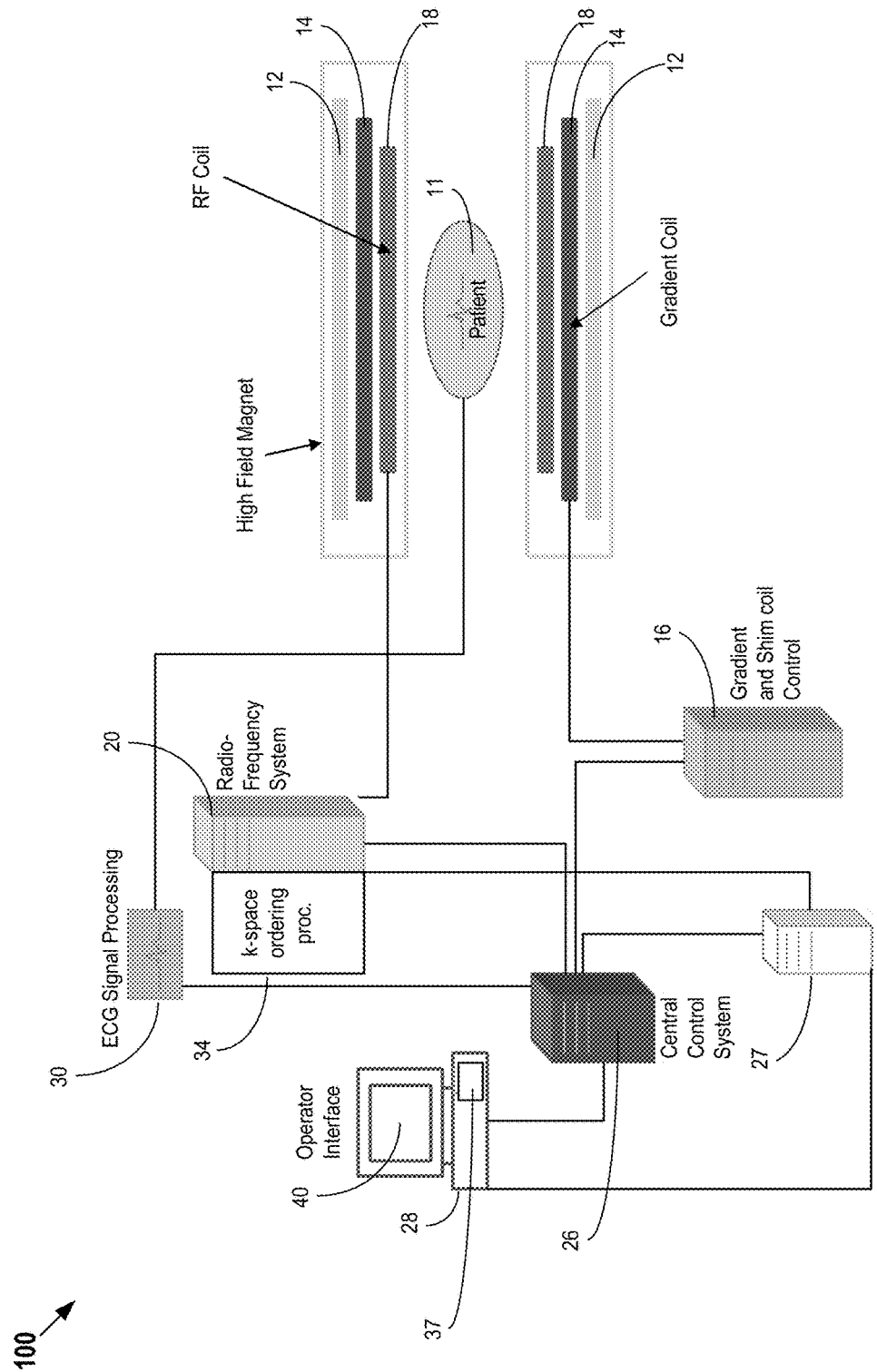
FIG. 1 shows a system for ordering acquisition of frequency domain components representing magnetic resonance image data for storage in a k-space storage array, as used by some embodiments of the present invention.

FIG. 1 shows a system 100 for ordering acquisition of frequency domain components representing MRI data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further, radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of a magnetic resonance dataset representing an magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and the magnetic field gradient change between successively acquired frequency components is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques may be used for reconstruction. For example, as described in greater detail below, an optimization algorithm is applied to iteratively solve a cost function which results in the reconstructed image.

Figure 2:
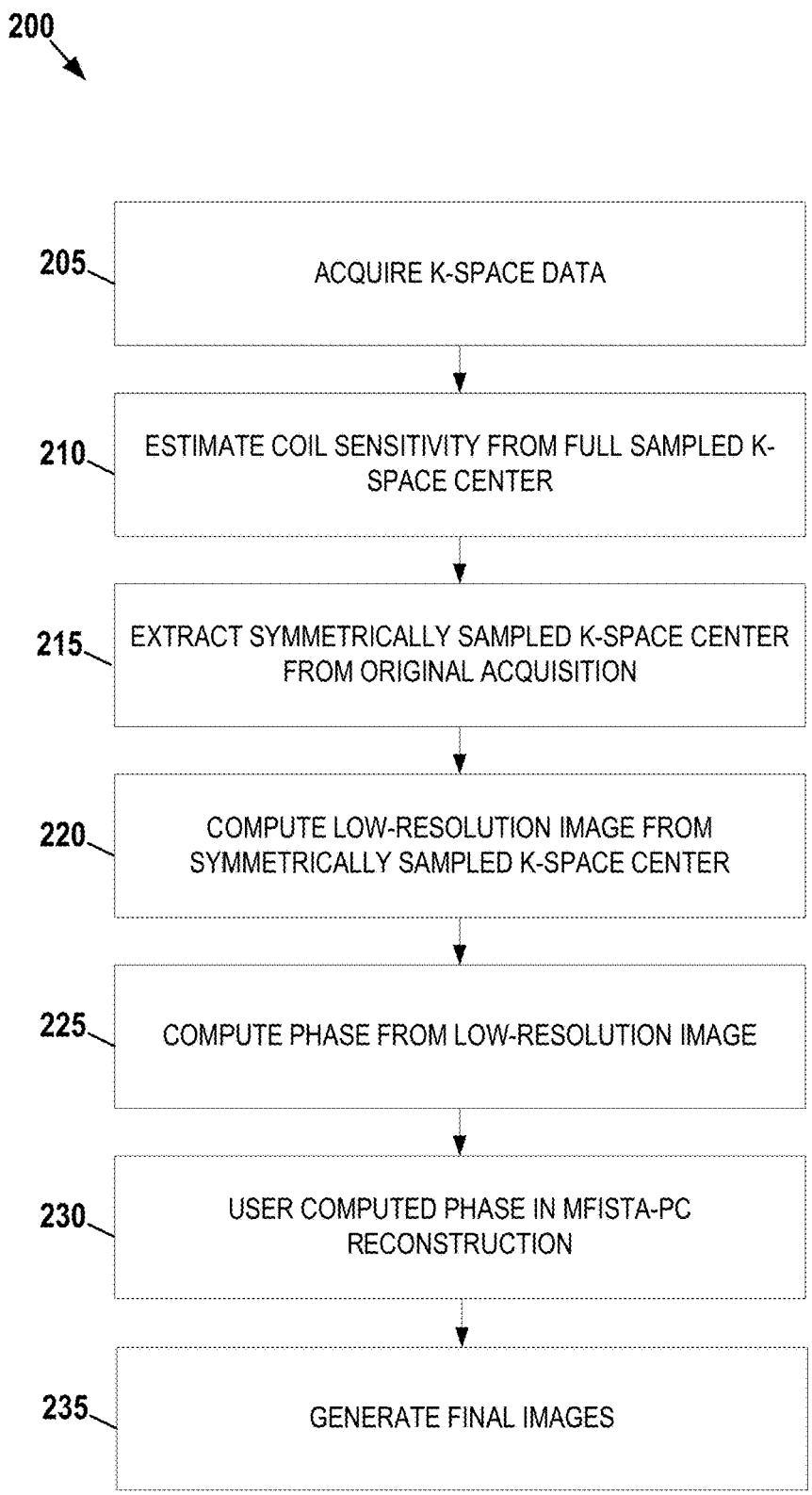
FIG. 2 provides an illustration of a process for a partial Fourier acquisition performing fast Sensitivity Encoding (SENSE)-based iterative sparse reconstruction, according to some embodiments.

FIG. 2 provides an illustration of a process 200 for a partial Fourier acquisition performing fast Sensitivity Encoding (SENSE)-based iterative sparse reconstruction, according to some embodiments. At step 205, k-space data is acquired using an MM system (see, e.g., FIG. 1). In some embodiments, the acquisition is performed using a Partial Fourier MR image acquisition technique where only a part of k-space is acquired and the respective conjugate-symmetric points are not acquired. This is different from k-space undersampling, because a contiguous block of k-space samples (usually in either the positive or the negative phases) is skipped, whereas k-space undersampling only skips samples that are scattered throughout the entire k-space. In other embodiments, the acquisition performed at step 205 is a standard MR image acquisition where the entire k-space is acquired or an undersampling mask with sampling locations that cover the entire k-space. It should be noted that the techniques described herein are not limited to the case when partial Fourier acquisitions happens in the phase-encoding directions. The same approach can also be applied to partial Fourier acquisition in the frequency-encoding directions. Such acquisition is widely used in cardiac and abdomen imaging.

Continuing with reference to FIG. 2, at step 210, coil sensitivity maps S are estimated from the fully sampled k-space center for the coils in the MM system, using any technique generally known in art. Next, at step 215, the symmetric part of the k-space center $y_0$ is extracted from the original data and passed to a closed-form least-squares problem as the measurement data y. Here, $y_0$ includes the values of k-space center, zero-padded to be the same size as the complete measurement data y. The amount of data available in $y_0$ depends on factors such as the effective echo time of sequence used to acquire the measurements. For example, for SPACE sequences, the size of $y_0$ is typically 24×24. Next, at step 220, image $x_0$ may be solved as follows:

$$x_0 = \sum_{c=1}^{N_c} S_c{}^\wedge H \cdot F^{-1}(y_0) \quad (1)$$

where $S_c$ is the coil sensitivity from coil c. The output of Equation 1 is a low resolution reconstruction image.

The phase p of image reconstructed at step 220 is the phase that will be used in later steps of the process 200. Thus, at step 225 the phase p is computed from the low-resolution image $x_0$ as follows:

$$p = \exp(i \angle x_0) \quad (2)$$

The low resolution image is served as the initial estimate in step 230 (discussed below). The reason that the phase term is obtained from the above closed-form method rather than a direct Fourier transform is to let the phase term match with the phase of the coil sensitivities, because the same coil sensitivities are used by the reconstruction in step 230.

At step 230, the entire partial k-space data is passed to the Modified Fast Iterative Shrinkage Thresholding Algorithm (mFISTA) reconstruction algorithm, with the low resolution $x_0$ from step 225 used as the initial estimate of the image. Within each iteration, after obtaining the solution from the proximal operator, the phase of the estimate is replaced by the phase term computed at step 225. Various types of proximal algorithms generally known in the art may be used during each iteration including, for example, the Chambolle-Pock algorithm and the Dykstra Algorithm. Finally, at step 235, the final images are generated based on the reconstructed data.

FIG. 3 illustrates an algorithm 300 for mFISTA with Phase Correction (mFISTA-PC) that may be applied at step 230, according to some embodiments. In this algorithm 300, y is the complete k-space sample, A is the forward transform (i.e., the Fourier transform and the coil sensitivity), L is the Lipschitz constant, λ is a regularization constant, $x_0$ is the low resolution image, and p is the corresponding phase. The algorithm 300 presented in FIG. 3 is similar to the conventional image reconstruction algorithm Fast Iterative Shrinkage Thresholding Algorithm (FISTA); however, after the application of the proximal algorithm (e.g., Chambolle-Pock) the magnitude of the image is multiplied by the phase from the low-resolution image. Note that it is assumed that phase is usually of low-resolution, thus the phase extracted from the low-resolution initial estimate of the image can be sufficiently assumed to be the phase of the final image.

FIG. 4 illustrates an algorithm 400 for mFISTA with attenuated Phase Correction (mFISTA-APC) that may alternatively be applied at step 230, according to some embodiments. The algorithm 400 presented in FIG. 4 is similar to the algorithm 300 shown in FIG. 3, except that phase correction is attenuated. Specifically, the phase correction step is only performed for a predetermined number of iterations of the reconstruction algorithm, to guarantee a proper convergence of the reconstruction of the image magnitude. In the example of FIG. 4, this predetermined number is set to 10; however, in principle, other predetermined numbers may alternatively be used in other embodiments.

In other embodiments, another alternative algorithm may be applied at step 230 wherein a phase constraint is applied with adaptive weighting. More specifically, a penalized phase constraint term is added to the reconstruction objective function to replace the phase correction, which is weighted independently for each spatial location. The constraint is adaptively weighted with higher weights at spatial locations with high phase variations and lower weights at spatial locations with low phase variations. Thus, for the cost function $$\operatorname*{argmin}_{x} \frac{1}{2}\|y - Ax\|_2^2 + \lambda\|x\|_1 + \beta R\|x - |x|\|_1 \quad (3)$$

the terms $\beta R\|x - |x|\|_1$ represent a phase constraint term which penalizes the difference between the image and its magnitude, thus enforcing the image to be real positive. In this equation, β is a scalar regularization parameter and R is the spatial adaptive weighting computed from the previous iteration of image output. This cost function can be solved with a non-linear optimization algorithm.

The techniques described herein can be used and extended to any partial Fourier reconstruction in both 2D and 3D MRI use cases with or without dynamic imaging. The conventional mFISTA reconstruction has shown promising results and is used in works-in-progress packages from several clinical partners. However, partial Fourier acquisition had to be avoided so far, especially for sequences such as SPACE. SPACE is typically used in musculoskeletal, neurological, and body applications, and a large part relies on partial Fourier acquisition to achieve a suitable effective echo time (TE) and an acceptable acquisition time. The same holds true for the turbo spin echo (TSE) sequence, which is one of the most heavily used sequences in clinical MRI. Therefore, the techniques described herein, which enables partial Fourier reconstruction, will be a strong addition to the existing reconstruction pipeline.

Figure 5A:
FIG. 5A shows the transverse-plane from de-coupled reconstruction of an example volunteer knee scan performed without partial Fourier techniques.
Figure 5B:
FIG. 5B provides the transverse-plane from de-coupled reconstruction of an example volunteer knee scan performed using partial Fourier acquisition with mFISTA reconstruction, according to different embodiments.
Figure 5C:
FIG. 5C provides the transverse-plane from de-coupled reconstruction of an example volunteer knee scan performed using a partial Fourier acquisition with mFISTA-PC reconstruction, according to different embodiments.
Figure 6A:
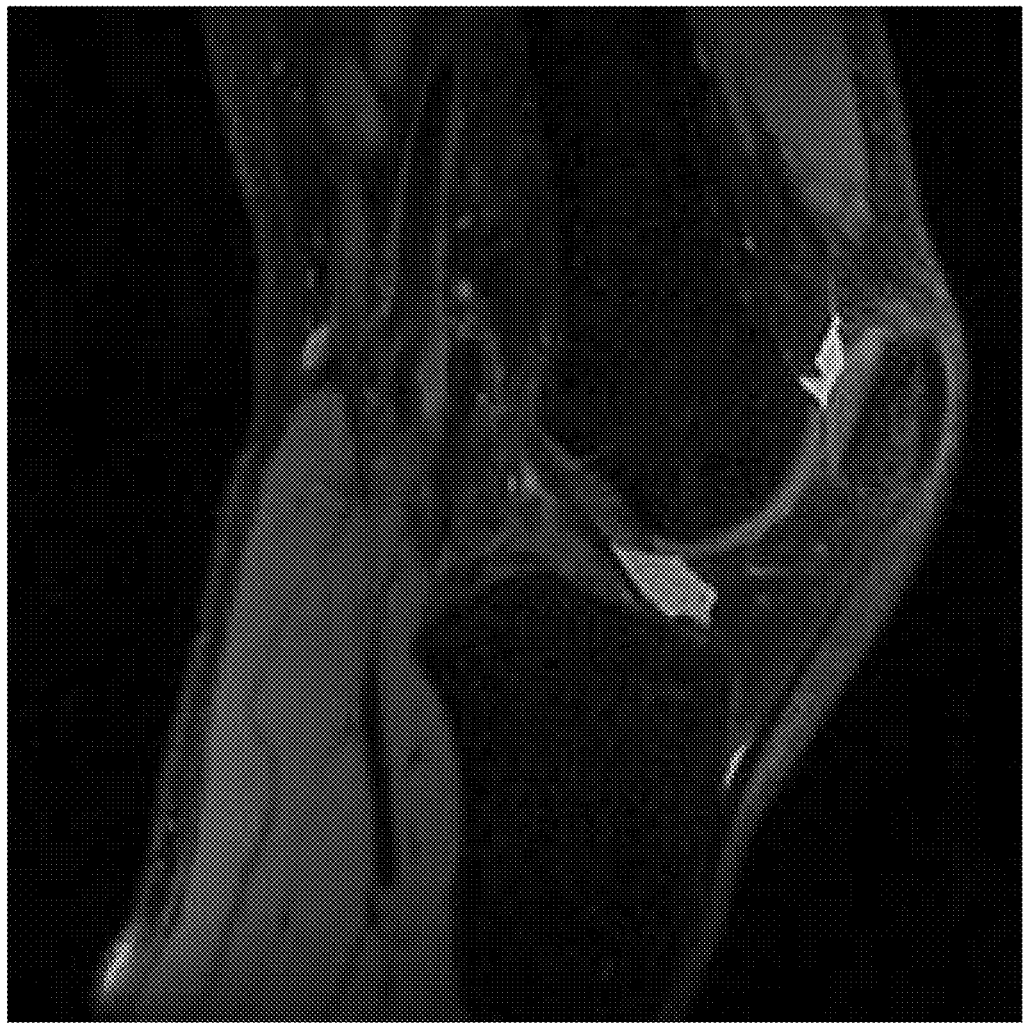
FIG. 6A provides the sagittal-plane from coupled reconstruction of an example volunteer knee scan performed without partial Fourier techniques.
Figure 6B:
FIG. 6B provides the sagittal-plane from coupled reconstruction of an example volunteer knee scan performed using partial Fourier acquisition with mFISTA reconstruction, according to different embodiments.
Figure 6C:
FIG. 6C provides the sagittal-plane from coupled reconstruction of an example volunteer knee scan performed using a partial Fourier acquisition with mFISTA-PC reconstruction.

FIG. 2 provides an illustration of a process 200 for a partial Fourier acquisition performing fast Sensitivity Encoding (SENSE)-based iterative sparse reconstruction, according to some embodiments. FIG. 3 illustrates an algorithm 300 for mFISTA with Phase Correction (mFISTA-PC) that may be applied at step 230, according to some embodiments. FIG. 4 illustrates an algorithm 400 for mFISTA with attenuated Phase Correction (mFISTA-APC) that may alternatively be applied at step 230, according to some embodiments. FIGS. 5A-5C and 6A-6C show an example of a volunteer knee scan with the SPACE sequence described herein, as it may be implemented in some embodiments. More specifically, FIGS. 5A-5C provide the transverse-plane from de-coupled reconstruction and FIGS. 6A-6C provide the sagittal-plane from coupled reconstruction. FIG. 5A and FIG. 6A provide images showing the original dataset that was acquired without partial Fourier techniques. FIG. 5B and FIG. 6B show a partial Fourier acquisition with mFISTA reconstruction. In the images shown in FIG. 5B and FIG. 6B, part of the k-space was retrospectively filled with zeroes. Note that mFISTA reconstruction results in a blurry image for this example. Finally, the images in FIG. 5C and FIG. 6C show the results of a partial Fourier acquisition with mFISTA-PC reconstruction (see, e.g., FIG. 3) which restores the sharpness of the original dataset.

Figure 7:
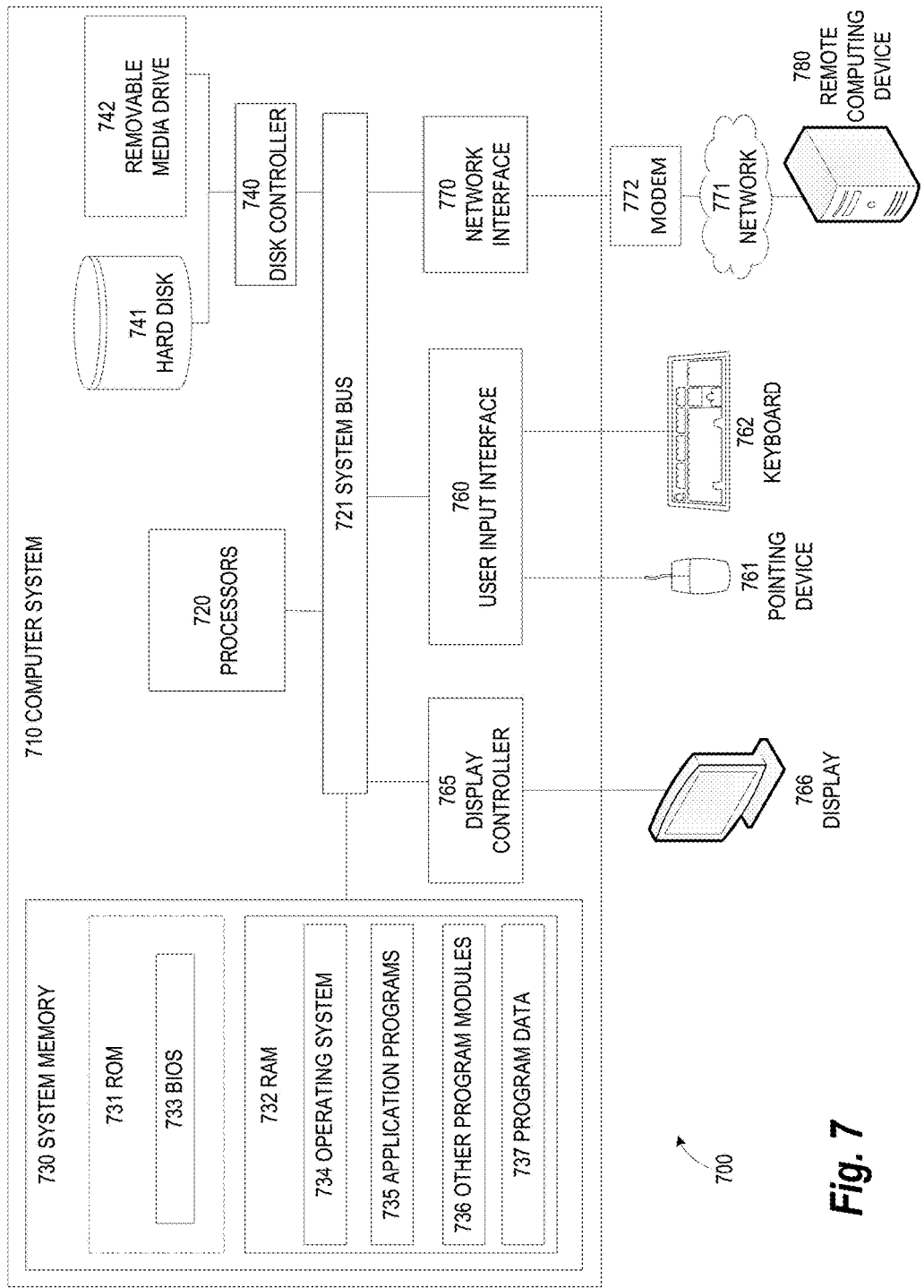
FIG. 7 illustrates an exemplary computing environment 700 within which embodiments of the invention may be implemented.

FIG. 7 illustrates an exemplary computing environment 700 within which embodiments of the invention may be implemented. For example, this computing environment 700 may be used to implement the process 200 described in FIG. 2 as well as the algorithms described in FIGS. 3 and 4. In some embodiments, the computing environment 700 may be used to implement one or more of the components illustrated in the system 100 of FIG. 1. The computing environment 700 may include computer system 710, which is one example of a computing system upon which embodiments of the invention may be implemented. Computers and computing environments, such as computer system 710 and computing environment 700, are known to those of skill in the art and thus are described briefly here.

As shown in FIG. 7, the computer system 710 may include a communication mechanism such as a bus 721 or other communication mechanism for communicating information within the computer system 710. The computer system 710 further includes one or more processors 720 coupled with the bus 721 for processing the information. The processors 720 may include one or more central processing units (CPUs), graphical processing units (GPUs), or any other processor known in the art.

The computer system 710 also includes a system memory 730 coupled to the bus 721 for storing information and instructions to be executed by processors 720. The system memory 730 may include computer readable storage media in the form of volatile and/or nonvolatile memory, such as read only memory (ROM) 731 and/or random access memory (RAM) 732. The system memory RAM 732 may include other dynamic storage device(s) (e.g., dynamic RAM, static RAM, and synchronous DRAM). The system memory ROM 731 may include other static storage device(s) (e.g., programmable ROM, erasable PROM, and electrically erasable PROM). In addition, the system memory 730 may be used for storing temporary variables or other intermediate information during the execution of instructions by the processors 720. A basic input/output system (BIOS) 733 containing the basic routines that help to transfer information between elements within computer system 710, such as during start-up, may be stored in ROM 731. RAM 732 may contain data and/or program modules that are immediately accessible to and/or presently being operated on by the processors 720. System memory 730 may additionally include, for example, operating system 734, application programs 735, other program modules 736 and program data 737.

The computer system 710 also includes a disk controller 740 coupled to the bus 721 to control one or more storage devices for storing information and instructions, such as a hard disk 741 and a removable media drive 742 (e.g., floppy disk drive, compact disc drive, tape drive, and/or solid state drive). The storage devices may be added to the computer system 710 using an appropriate device interface (e.g., a small computer system interface (SCSI), integrated device electronics (IDE), Universal Serial Bus (USB), or FireWire).

The computer system 710 may also include a display controller 765 coupled to the bus 721 to control a display 766, such as a cathode ray tube (CRT) or liquid crystal display (LCD), for displaying information to a computer user. The computer system includes an input interface 760 and one or more input devices, such as a keyboard 762 and a pointing device 761, for interacting with a computer user and providing information to the processor 720. The pointing device 761, for example, may be a mouse, a trackball, or a pointing stick for communicating direction information and command selections to the processor 720 and for controlling cursor movement on the display 766. The display 766 may provide a touch screen interface which allows input to supplement or replace the communication of direction information and command selections by the pointing device 761.

The computer system 710 may perform a portion or all of the processing steps of embodiments of the invention in response to the processors 720 executing one or more sequences of one or more instructions contained in a memory, such as the system memory 730. Such instructions may be read into the system memory 730 from another computer readable medium, such as a hard disk 741 or a removable media drive 742. The hard disk 741 may contain one or more datastores and data files used by embodiments of the present invention. Datastore contents and data files may be encrypted to improve security. The processors 720 may also be employed in a multi-processing arrangement to execute the one or more sequences of instructions contained in system memory 730. In alternative embodiments, hard-wired circuitry may be used in place of or in combination with software instructions. Thus, embodiments are not limited to any specific combination of hardware circuitry and software.

As stated above, the computer system 710 may include at least one computer readable medium or memory for holding instructions programmed according to embodiments of the invention and for containing data structures, tables, records, or other data described herein. The term "computer readable medium" as used herein refers to any medium that participates in providing instructions to the processor 720 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 741 or removable media drive 742. Non-limiting examples of volatile media include dynamic memory, such as system memory 730. Non-limiting examples of transmission media include coaxial cables, copper wire, and fiber optics, including the wires that make up the bus 721. Transmission media may also take the form of acoustic or light waves, such as those generated during radio wave and infrared data communications.

The computing environment 700 may further include the computer system 710 operating in a networked environment using logical connections to one or more remote computers, such as remote computer 780. Remote computer 780 may be a personal computer (laptop or desktop), a mobile device, a server, a router, a network PC, a peer device or other common network node, and typically includes many or all of the elements described above relative to computer system 710. When used in a networking environment, computer system 710 may include modem 772 for establishing communications over a network 771, such as the Internet. Modem 772 may be connected to bus 721 via user network interface 770, or via another appropriate mechanism.

Network 771 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 710 and other computers (e.g., remote computer 780). The network 771 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 771.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for sparse iterative phase correction for Magnetic Resonance (MR) partial Fourier reconstruction, the method comprising:
   acquiring a partial Fourier k-space dataset using an MR scanner;
   estimating, by a control computer, a coil sensitivity map associated with the MR scanner from fully sampled k-space center;
   extracting, by the control computer, a symmetrically sampled k-space center dataset from the partial Fourier k-space dataset;
   determining, by the control computer, a low-resolution image based on the symmetrically sampled k-space center dataset and the coil sensitivity map;
   determining, by the control computer, phase corresponding to the low-resolution image; and
   applying, by the control computer, an iterative reconstruction process to generate an image based on the partial Fourier k-space dataset, wherein the iterative reconstruction process applies a Fast Iterative Shrinkage Thresholding Algorithm (FISTA) with phase correction based on the phase corresponding to the low-resolution image.

2. The method of claim 1, wherein the iterative reconstruction process uses the low-resolution image as an initial estimate for the image.

3. The method of claim 2, wherein each respective iteration of the iterative reconstruction process comprises:

applying a proximal operator to determine an updated estimate for the image; and replacing a phase term in the updated estimate from the image with the phase corresponding to the low-resolution image.

4. The method of claim 3, wherein the proximal operator applies the Chambolle-Pock algorithm.

5. The method of claim 3, wherein the proximal operator applies the Dykstra algorithm.

6. The method of claim 2, wherein each respective iteration of the iterative reconstruction process comprises:

applying a proximal operator to determine an updated estimate for the image; and if less than a pre-defined number of iterations of the iterative reconstruction process have been completed, replacing a phase term in the updated estimate from the image with the phase corresponding to the low-resolution image.

7. The method of claim 1, wherein the partial Fourier k-space dataset is acquired in phase-encoding directions.

8. The method of claim 1, wherein the partial Fourier k-space dataset is acquired in frequency-encoding directions.

9. An article of manufacture for sparse iterative phase correction for Magnetic Resonance (MR) partial Fourier reconstruction, the article of manufacture comprising a non-transitory, tangible computer-readable medium holding computer-executable instructions for performing a method comprising:

receiving a partial Fourier k-space dataset acquired using an MR scanner;

estimating a coil sensitivity map associated with the MR scanner from fully sampled k-space center;

extracting a symmetrically sampled k-space center dataset from the partial Fourier k-space dataset;

determining a low-resolution image from the symmetrically sampled k-space center dataset;

determining phase corresponding to the low-resolution image; and applying an iterative reconstruction process to generate an image based on the partial Fourier k-space dataset, wherein the iterative reconstruction process applies a Fast Iterative Shrinkage Thresholding Algorithm (FISTA) with phase correction based on the phase corresponding to the low-resolution image.

10. The article of manufacture of claim 9, wherein the iterative reconstruction process uses the low-resolution image as an initial estimate for the image.

11. The article of manufacture of claim 10, wherein each respective iteration of the iterative reconstruction process comprises:

applying a proximal operator to determine an updated estimate for the image; and replacing a phase term in the updated estimate from the image with the phase corresponding to the low-resolution image.

12. The article of manufacture of claim 11, wherein the proximal operator applies the Chambolle-Pock algorithm.

13. The article of manufacture of claim 11, wherein the proximal operator applies the Dykstra algorithm.

14. The article of manufacture of claim 10, wherein each respective iteration of the iterative reconstruction process comprises:

applying a proximal operator to determine an updated estimate for the image; and if less than a pre-defined number of iterations of the iterative reconstruction process have been completed, replacing a phase term in the updated estimate from the image with the phase corresponding to the low-resolution image.

15. The article of manufacture of claim 9, wherein the partial Fourier k-space dataset is acquired in phase-encoding directions.

16. The article of manufacture of claim 9, wherein the partial Fourier k-space dataset is acquired in frequency-encoding directions.

17. A system for sparse iterative phase correction for Magnetic Resonance (MR) partial Fourier reconstruction, the system comprising:

an imaging device comprising a plurality of coils configured to acquire a partial Fourier k-space dataset acquired using a magnetic resonance imaging device; and a central computer configured to apply an iterative reconstruction process to generate an image based on the partial Fourier k-space dataset over a plurality of iterations, wherein the iterative reconstruction process applies a Fast Iterative Shrinkage Thresholding Algorithm (FISTA) with phase correction performed during at least a portion of the plurality of iterations.

18. The system of claim 17, wherein phase correction is performed during each of the plurality of iterations.

19. The system of claim 17, wherein the central computer is further configured to:

estimate a coil sensitivity map associated with the imaging device;

extract a symmetrically sampled k-space center dataset from the partial Fourier k-space dataset;

determining a low-resolution image based on the symmetrically sampled k-space center dataset and the coil sensitivity map; and determine phase corresponding to the low-resolution image, wherein the phase corresponding to the low-resolution image is used for the phase correction performed during each of the at least a portion of the plurality of iterations.

20. The system of claim 19, wherein the central control computer is configured to use the low-resolution image as an initial estimate of the image in the iterative reconstruction process.

* * * * *